United States Patent
Klar et al.

[11] Patent Number: 6,162,920
[45] Date of Patent: Dec. 19, 2000

[54] TAXANE DERIVATIVES HAVING A PYRIDYL SUBSTITUTED C13 SIDE CHAIN, THEIR PREPARATION AND THEIR USE AS ANTI-TUMOR AGENTS

[75] Inventors: Ulrich Klar; Günter Neef, both of Berlin; Hermann Graf, Freiburg im Breisgau, all of Germany

[73] Assignee: Schering Aktiensgesellschaft, Berlin, Germany

[21] Appl. No.: 09/117,506

[22] PCT Filed: Jan. 31, 1997

[86] PCT No.: PCT/EP97/00440

§ 371 Date: Jul. 30, 1998

§ 102(e) Date: Jul. 30, 1998

[87] PCT Pub. No.: WO97/28156

PCT Pub. Date: Aug. 7, 1997

[30] Foreign Application Priority Data

Jan. 31, 1996 [DE] Germany ............ 196 05 024

[51] Int. Cl.⁷ .............. A61K 31/44; C07D 405/04
[52] U.S. Cl. .............. 546/281.7; 546/281.7; 536/107; 536/109; 424/450
[58] Field of Search .............. 546/281.7; 514/281

[56] References Cited

U.S. PATENT DOCUMENTS

| | | | |
|---|---|---|---|
| 5,489,601 | 2/1996 | Holton et al. | 514/337 |
| 5,760,219 | 6/1998 | Holton et al. | 540/354 |

FOREIGN PATENT DOCUMENTS

| | | |
|---|---|---|
| 534 708 | 3/1993 | European Pat. Off. |
| 94/21252 | 9/1994 | WIPO |
| 95/13053 | 5/1995 | WIPO |
| 95/19994 | 7/1995 | WIPO |
| 96/00724 | 1/1996 | WIPO |

OTHER PUBLICATIONS

Sharma et al., "Pharmaceutical and Physical Properties of Paclitaxel (Taxol↑) Complexes with Cyclodextrin," *Journal of Pharmaceutical Sciences*, vol. 84, pp. 1223–1230 (1995).

(List continued on next page.)

*Primary Examiner*—Alan L. Rotman
*Attorney, Agent, or Firm*—Millen White Zelano & Branigan

[57] ABSTRACT

The invention relates to pharmacologically active compounds that have the ability to influence the polymerisation and depolymerisation of tubulin.

A range of natural mitosis toxins are used as anti-tumor agents or are in the process of being clinically tested. There are various classes of such mitosis toxins that either demonstrate their cytotoxic action by inhibiting the polymerisation of microtubules in the spindle system (for example, Vinca alkaloids, colchicine) or achieve their cytotoxic action by a GTP-independent increase in the polymerisation of the tubulin and by preventing the depolymerisation of microtubules (for example, taxol, taxoters).

Owing to their physico-chemical properties, hitherto not understood, and as a result of the characteristics of neoplastic cells, mitosis toxins have a certain selectivity for tumor cells, but there still remains a not inconsiderable cytotoxicity towards non-transformed cells. The search for more selective compounds that are easier to manufacture and—like the taxane class of substances—are able to inhibit the depolymerisation of microtubules, had, surprisingly, led to the discovery of borneol esters, as described in P 4416374.6 and 19513040.5. Structural modifications in that class of compounds have revealed a considerable potential for optimisation in respect of the action on microtubules. Outstanding results have been obtained, inter alia, by formal esterification of those broneols with an acid of the Sk-H type. By synthesising the taxol derivatives described herein, in which the isoserine chain of the taxol has been replaced by Sk, the intention was to study whether it is also possible in that class of substances to achieve an improved stabilisation of microtubules, compared with taxol.

9 Claims, 2 Drawing Sheets

OTHER PUBLICATIONS

Nicolaou et al., "Chemistry and Biology of Taxol," *Angew. Chem. Int. Ed. Engl.,* vol. 33, pp. 15–44 (1994).

Georg et al., "Heteroaromatic Taxol Analogues: The Chemistry and Biological Activities of 3'–Furyl and 3'–Pyridyl Substituted Taxanes," *Bioorganic & Medicinal Chemistry Letters,* vol. 4, No. 11, pp. 1381–1384 (1994).

TAXANE DERIVATIVES HAVING A PYRIDYL SUBSTITUTED C13 SIDE CHAIN, THEIR PREPARATION AND THEIR USE AS ANTI-TUMOR AGENTS

The invention relates to pharmacologically active compounds that have the ability to influence the polymerisation and depolymerisation of tubulin.

A range of natural mitosis toxins are used as anti-tumour agents or are in the process of being clinically tested. There are various classes of such mitosis toxins that either demonstrate their cytotoxic action by inhibiting the polymerisation of microtubules in the spindle system (for example, Vinca alkaloids, colchicine) or achieve their cytotoxic action by a GTP-independent increase in the polymerisation of the tubulin and by preventing the depolymerisation of microtubules (for example, taxol, taxoters).

Owing to their physico-chemical properties, hitherto not understood, and as a result of the characterstics of neoplastic cells, mitosis toxins have a certain selectivity for tumour cells, but there still remains a not inconsiderable cytotoxicity towards non-transformed cells. The search for more selective compounds that are easier to manufacture and—like the taxane class of substances—are able to inhibit the depolymerisation of microtubules, had, surprisingly, led to the discovery of borneol esters, as described in P 4416374.6 and 19513040.5. Structural modifications in that class of compounds have revealed a considerable potential for optimisation in respect of the action on microtubules. Outstanding results have been obtained, inter alia, by formal esterification of those borneols with an acid of the Sk-H type. By synthesising the taxol derivatives described herein, in which the isoserine chain of the taxol has been replaced by Sk, the intention was to study whether it is also possible in that class of substances to achieve an improved stabilisation of microtubules, compared with taxol.

Further, the following documents disclose compounds showing pharmacological activity:
WO-A-94 21 252
Bioorg. Med. Chem. Lett. (1994) 4(11), 1381–1384
EP-A-0 534 708
Angew. Chem. Int. Ed. Engl. (1994) 33(1), 15–44
WO-A 95 13 053
WO-A-95 19 994
J. Pharm. Sci. (1995) 84(10), 1223–1230
WO-A-96 00 724

However, compounds disclosed in WO-A-94 21 252 form the closest state of the art.

Surprisingly, it has now been found that the compounds of formula I according to the invention, compared with taxol and state of the art compounds, have an advantageously altered activity profile. In addition to a clearly improved stabilisation of microtubules, the compounds of formula I demonstrate an additional influence on the polymerisation of tubulin.

The taxanes according to the invention are characterised by the general formula I wherein Sk may be $R^1$ may be hydrogen or $C_1$–$C_{10}$acyl, $R^2$ may be α-OH or β-OH, $R^3$ may be $C_1$–$C_{10}$alkyl, X-substituted phenyl, $C_1$–$C_{10}$alkoxy, X may be hydrogen, halogen, —$N_3$ or —CN, and free hydroxy groups in I may be functionally modified further by etherification or esterification, and also the α-, β- and γ-cyclodextrin clathrates thereof, and also compounds of the general formula I encapsulated with liposomes.

There come into consideration as alkyl group $R^3$ straight-chained or branched alkyl groups having from 1 to 10 carbon atoms, such as, for example, methyl, ethyl, propyl, isopropyl, butyl, isobutyl, tert-butyl, pentyl, isopentyl, neopentyl, heptyl, hexyl and decyl. Alkyl groups having from 1 to 4 carbon atoms are preferred. The acyl and alkoxy groups contained in $R^1$ and $R^3$, respectively, of general formula I contain from 1 to 10 carbon atoms, with formyl, acetyl, propionyl and isopropionyl groups, and methoxy, ethoxy, propoxy, isopropoxy and t-butoxy groups, respectively, being preferred.

Halogen in the definition of X is fluorine, chlorine, bromine or iodine.

Preferred compounds of the general formula I are:

3'-desphenyl-3'-(4-pyridyl)-3'-N-debenzoyl-3'-N-methoxycarbonyl-taxol,

3'-desphenyl-3'-(4-pyridyl)-3'-N-debenzoyl-3'-N-methoxycarbonyl-7-epi-taxol,

3'-desphenyl-3'-(4-pyridyl)-2,3'-N-bisdebenzoyl-3'-N-methoxycarbonyl-taxol, and

3'-desphenyl-3'-(4-pyridyl)-3'-N-debenzoyl-3'-N-methoxycarbonyl-10-desacetyl-taxol.

The invention relates also to a process for the preparation of borneol derivatives of formula I, which process is characterised in that an alcohol of the general formula II

II wherein R¹ and R² are as defined hereinabove and hydroxy groups contained in II are optionally protected, is reacted with a compound of the general formula IIIa, IIIb or IIIc, IIIa IIIb IIIc wherein R³ is as defined hereinabove and X' may be hydroxy, O-alkyl or halogen, and wherein free hydroxy groups are protected by etherification or esterification, to form compounds of the general formula I in which free hydroxy groups may be functionally modified further by etherification or esterification.

For the esterification of the alcohol function in II, deprotonation is carried out with a base, such as, for example, a metal hydride (for example sodium hydride), an alkali metal alcoholate (for example sodium methanolate, potassium tert-butanolate), an alkali metal hexamethyldisilazane (for example sodium hexamethyldisilazane), 1,5-diazabicyclo[4.3.0]non-5-ene (DBN), 1,8-diazabicyclo[5.4.0]undec-7-ene (DBU), triethylamine, 4-(dimethylamino)pyridine (DMAP) or 1,4-diazabicyclo[2.2.2]octane (DABCO) and reaction is carried out with a carboxylic acid derivative of the general formula III in an inert solvent, such as, for example, dichloromethane, diethyl ether, or tetrahydrofuran, at from −70° C. to +50° C. The preferred reaction is with sodium hydride as base, a cyclic acid amide as carboxylic acid derivative and tetrahydrofuran as solvent at temperatures of from −10° C. to +25° C.

Free hydroxy groups in I may be functionally modified further in accordance with methods known to a person skilled in the art, for example by etherification or esterification. For example, free hydroxy groups may be converted into pyridinium salts with physiologically tolerable acids, into phosphates or salts thereof with physiologically tolerable bases or into esters thereof, into sulphates or salts thereof with physiologically tolerable bases or into esters thereof, or into esters and ethers with water-soluble polymers. Ethers and esters of compounds that are themselves able to demonstrate tumour-inhibiting action can also be prepared.

Biological effects and fields of use of the novel taxol derivatives:

The novel compounds of formula I are valuable drugs. They interact with tubulin by influencing the polymerisation of tubulin and stabilising microtubules that have formed and are thus able to influence cell division in a phase-specific manner. That affects, especially, rapidly growing neoplastic cells, the growth of which is largely uninfluenced by intercellular regulating mechanisms. Active ingredients of that type are, in principle, suitable for the treatment of disorders in which influence on cell division may be indicated therapeutically.

There may be mentioned by way of example the treatment of malignant tumours, malaria, the treatment of disorders caused by gram-negative bacteria, and also the treatment of disorders of the central and peripheral nervous system that are based on excitotoxic mechanisms, such as, for example, the treatment of acute neurodegenerative symptoms, such as arise, for example, as a result of stroke or traumatic brain injuries, the treatment of chronic neurodegenerative symptoms including Alzheimer's disease, and also the treatment of amyotrophic lateral sclerosis.

There may be mentioned as a field of use for malignant tumours, for example, the treatment of ovarian, stomach, colonic, adeno, breast, lung, head and neck carcinomas, malignant melanoma and acute lymphocytic and myelocytic leukaemia.

The compounds according to the invention may be used generally on their own or, to obtain additive or synergistic effects, in combination with other active principles and classes of substances that may be used in the fields of therapy in question.

Taking the example of tumour therapy, there may be mentioned the combination with platinum complexes, such as, for example, cisplatin and carboplatin, intercalating substances, for example, from the class of the anthracyclines, such as, for example, doxorubicin, or from the class of the anthrapyrazoles, such as, for example, Cl-941, substances that interact with tubulin, for example from the class of the Vinca alkaloids, such as, for example, vincristine and vinblastine, or from the novel class of the borneol esters described in P 4416374.6 and 19513040.5, or from the class of the macrolides, such as, for example, rhizoxin, or other compounds, such as, for example, colchicine, combretastatin A-4 and epothilon A and B, DNA topoisomerase inhibitors, such as, for example, camptothecin, etoposide, topotecan and teniposide, folate or pyrimidine antimetabolites, such as, for example, lometrexol and gemcitubin, DNA alkylating compounds, such as, for example, adozelesin and dystamycin A, growth factor inhibitors (for example, inhibitors of PDGF, EGF, TGFb, EGF), such as, for example, somatostatin, suramin, bombesin antagonists, inhibitors of tyrosine protein kinase or of the protein kinases A and C, such as, for example, erbstatin, genistein, staurosporine, ilmofosin and 8-Cl-cAMP, anti-hormones from the class of the antigestagens, such as, for example, mifepristone, onapristone or from the class of the anti-oestrogens, such as, for example tamoxifen, or from the class of the anti-androgens, such as, for example, cyproterone acetate, metastasis-inhibiting compounds, for example, from the class of the eicosanoids, such as, for example, $PGI_2$, $PGE_1$, 6-oxo-$PGE_1$ and stable derivatives thereof (for example iloprost, cicaprost, beraprost), inhibitors of trans-membrane $Ca^{2+}$ influx, such as, for example, verapamil, galopamil, flunarizine, diltiazem, nifedipine and nimodipine, neuroleptics, such as, for example, chlorpromazine, trifluoperazine, thioridazine and perphenazine, local anaesthetics, such as, for example, carbanilate-Ca7, cinchocaine, carbanilate-$Ca_3$, articaine, carbanilate, lidocaine, angiogenesis-inhibiting substances, such as, for example, anti-VEGF antibodies, endostatin B, interferon a, AGM 1470, and inhibitors of cell proliferation in psoriasis, Kaposi's sarcoma and neuroblastoma.

The invention relates also to medicaments based on compounds of the general formula I that are pharmaceutically acceptable, that is to say compounds that are not toxic in the doses used, optionally together with customary excipients, carriers and additives.

The compounds according to the invention may be processed in accordance with methods of galenic pharmacy known per se to pharmaceutical preparations for enteral, percutaneous, parenteral or local administration. They may be administered in the form of tablets, dragées, gelatin capsules, granules, suppositories, implants, injectable, sterile aqueous or oily solutions, suspensions or emulsions, ointments, creams and gels. The invention therefore relates also to the use of the compounds according to the invention in the preparation of medicaments.

The active ingredient(s) may be mixed with excipients that are customary in galenic pharmacy, such as, for example, gum arabic, talc, starch, mannitol, methylcellulose, lactose, surfactants such as Tweens or Myrj, magnesium stearate, aqueous or non-aqueous carriers, paraffin derivatives, wetting, dispersing, emulsifying and preserving agents, and flavourings to adjust the taste (for example ethereal oils).

The invention therefore relates also to pharmaceutical compositions and medicaments that contain at least one compound according to the invention as active ingredient. A unit dose contains approximately from 0.1 to 100 mg of active ingredient(s). The dosage of the compounds according to the invention in humans is approximately from 0.1 to 1000 mg per day.

The following Examples serve to explain further the preparation of the compounds according to the invention.

EXAMPLE 1

3'-Desphenyl-3'-(4-pyridyl)-3'-N-debenzoyl-3'-N-methoxycarbonyl-taxol 8.6 μl of a 1M solution of tetrabutylammonium fluoride in tetrahydrofuran are added at 3° C., under an atmosphere of dry argon, to a solution of 3.1 mg (2.9 μmol) of the compound prepared in accordance with Example 1a in 0.5 ml of anhydrous tetrahydrofuran, and the reaction mixture is stirred for 30 minutes. The mixture is poured into a saturated sodium hydrogen carbonate solution and extraction is carried out with dichloromethane, the organic extract is concentrated and the residue is purified by chromatography on one half of an analytical thin-layer plate. Ethyl acetate is used as mobile phase and a mixture of dichloromethane and methanol is used as eluting agent. 0.4 mg (0.5 μmol, 17%) of the title compound is isolated.

$^1$H-NMR (CDCl$_3$): d=1.16 (3H), 1.25 (3H), 1.70 (3H), 1.75 (1H), 1.84 (3H), 1.90 (1H), 2.26 (3H), 2.25–2.38 (2H), 2.38 (3H), 2.48 (1H), 2.56 (1H), 3.62 (3H), 3.81 (1H), 4.19 (1H), 4.31 (1H), 4.40 (1H), 4.71 (1H), 4.95 (1H), 5.37 (1H), 5.66 (1H, 5.69 (1H), 6.28 (1H), 6.31 (1H), 7.40 (2H), 7.51 (2H), 7.61 (1H), 8.11 (2H), 8.66 (2H) ppm.

EXAMPLE 1a

2'-Triisopropylsilyl-3'-desphenyl-3'-(4-pyridyl)-3'-N-debenzoyl-3'-N-methoxycarbonyl-7-triethylsilyl-taxol 12 mg of an approximately 60% sodium hydride dispersion are added at 3° C., under an atmosphere of dry argon, to a solution of 4.2 mg (6.0 μmol) and 11.4 mg of the compounds prepared in accordance with Examples 1b and 1c in 0.1 ml of anhydrous tetrahydrofuran, and the mixture is heated to 30° C. and stirred for 30 minutes. The mixture is cooled again to 3° C., 30% aqueous acetic acid is added and extraction is carried out several times with diethyl ether. The combined organic extracts are washed with a saturated sodium chloride solution and dried over magnesium sulphate. After filtration and removal of solvent, the residue is purified by chromatography on two analytical thin-layer plates. A mixture of n-hexane and ethyl acetate is used as mobile phase, and a mixture of dichloromethane and methanol is used as eluting agent. 3.7 mg (3.4 μmol, 57%) of the title compound are isolated.

$^1$H-NMR (CDCl$_3$): d=0.60 (6H), 0.80–1.02 (30H), 1.25 (6H), 1.70 (3H), 1.91 (1H), 2.03 (3H), 2.14 (1H), 2.20 (3H), 2.36 (1H), 2.49 (3H), 2.53 (1H), 3.54 (3H), 3.84 (1H), 4.18 (1H), 4.30 (1H), 4.49 (1H), 4.85 (1H), 4.93 (1H), 5.30 (1H), 5.60 (1H), 5.70 (1H), 6.32 (1H), 6.47 (1H), 7.28 (2H), 7.49 (2H), 7.59 (1H), 8.13 (2H), 8.64 (2H) ppm.

EXAMPLE 1b

7-Triethylsilyl-baccatin III

21 μl of triethylchlorosilane and 10.3 mg of imidazole are added at 3° C., under an atmosphere of dry argon, to a solution of 3.7 mg (6.3 μmol) of chromatographically purified baccatin III (Calbiochem Corp.) in 0.3 ml of anhydrous dimethylformamide, and the reaction mixture is stirred for one hour. The mixture is poured into a saturated sodium hydrogen carbonate solution, extraction is carried out several times with diethyl ether followed by washing with a saturated sodium chloride solution, and the combined organic extracts are concentrated. The residue obtained after filtration and removal of solvent is purified by chromatography on one half of an analytical thin-layer plate. A mixture of n-hexane and ethyl acetate is used as mobile phase, and a mixture of dichloromethane and methanol is used as eluting agent 3.0 mg (5.6 μmol, 88%) of the title compound are isolated.

$^1$H-NMR (CDCl$_3$): d=0.59 (6H), 0.92 (9H), 1.06 (3H), 1.20 (3H), 1.62 (1H), 1.69 (3H), 1.88 (1H), 2.04 (1H), 2.19 (6H), 2.28 (2H), 2.29 (3H), 2.53 (1H), 3.88 (1H), 4.14 (1H), 4.31 (1H), 4.50 (1H), 4.83 (1H), 4.98 (1H), 5.63 (1H), 6.47 (1H), 7.49 (2H), 7.61 (1H), 8.11 (2H) ppm.

EXAMPLE 1c

(3R,4S)-1-(Methoxycarbonyl)-3-triisopropylsilyloxy-4-(4-pyridyl)-2-azetidinone 573 mg of 4-dimethylaminopyridine and 193 μl of chloroformic acid methyl ester are added at 3° C., under an atmosphere of dry argon, to a solution of 250 mg (0.78 mmol) of the compound prepared in accordance with Example 1d in 10 ml of anhydrous dichloromethane and the reaction mixture is heated to 23° C. and stirred for a further 16 hours. The mixture is poured into a saturated ammonium chloride solution, extraction is carried out several times with diethyl ether followed by washing with a saturated sodium chloride solution, and the combined organic extracts are concentrated. The residue obtained after filtration and removal of solvent is purified by chromatography on approximately 150 ml of fine silica gel using a mobile phase mixture of n-hexane and ethyl acetate. 251 mg (0.66 mmol, 85%) of the title compound are isolated.

$^1$H-NMR (CDCl$_3$): d=0.82–1.07 (21H), 3.82 (3H), 5.11 (1H), 5.26 (1H), 7.23 (2H), 8.61 (2H) ppm.

EXAMPLE 1d

(3R,4S)-3Triisopropylsilyloxy-4-(4-pyridyl)-2-azetidinone

A solution of 67.3 g of ceric ammonium nitrate in 700 ml of water is added at 3° C., under an argon atmosphere, to a solution of 17.2 g (40.3 mmol) of the compound prepared in accordance with Example 1e in 384 ml of acetonitrile, and the reaction mixture is stirred for 30 minutes. The mixture is poured into a saturated sodium hydrogen carbonate solution, extraction is carried out several times with ethyl acetate, and the combined organic extracts are washed with a 1% sodium hydroxide solution and dried over magnesium sulphate. The residue obtained after filtration and removal of solvent is purified by chromatography on approximately 800 ml of fine silica gel using a mobile phase mixture of n-hexane and ethyl acetate. 7.89 g (24.6 mmol, 61%) of the title compound are isolated.

$^1$H-NMR (CDCl$_3$): d=0.78–1.07 (21H), 4.81 (1H), 5.23 (1H), 6.39 (1H), 7.28 (2H 8.59 (2H) ppm.

EXAMPLE 1e

(3R,4S)-1-(4-Methoxyphenyl)-3-triisopropylsilyloxy-4-(4-pyridyl)-2-azetidinone A solution of 12.6 ml of freshly distilled diisopropylamine in 70 ml of anhydrous tetrahydrofuran is cooled to −30° C. under an atmosphere of dry argon, 37.6 ml of a 2.4M solution of n-butyllithium in n-hexane are added and the mixture is heated to 0° C. After 30 minutes, the mixture is cooled to −78° C., a solution of 22.1 g (56.6 mmol) of (1R,2S)-2-phenyl-1-cyclohexyl-triisopropylsilyloxyacetate, prepared analogously to the process described in Tetrahedron Vol. 48, No. 34, pp. 6985–7012, 1992, in 70 ml of anhydrous tetrahydrofuran is added dropwise thereto and the mixture is stirred for 3 hours. A solution of 15.6 g (73.5 mmol) of the aldimine prepared in accordance with Example 1f in 150 ml of anhydrous tetrahydrofuran is then added and the mixture is heated to 23° C. in the course of 16 hours. The mixture is poured into a saturated ammonium chloride solution, extraction is carried out several times with ethyl acetate followed by washing with a saturated sodium chloride solution, and the combined organic extracts are concentrated. The residue obtained after filtration and removal of solvent is purified by chromatography on approximately 1.8 liters of fine silica gel using a mobile phase mixture of n-hexane and ethyl acetate. 17.2 g (40.3 mmol, 71%) of the title compound are isolated.

$^1$H-NMR(CDCl$_3$): d=0.82–1.12 (21H), 3.76 (3H), 5.12 (1H), 5.29 (1H), 6.80 (2H), 7.19–7.30 (4H), 8.60 (2H) ppm.

EXAMPLE 1f

N-(4-Methoxyphenyl)-(4-pyridyl)aldimine 7.8 ml of pyridine-4-aldehyde and 8.4 g of magnesium sulphate are added, under an atmosphere of dry argon, to a solution of 10 g (81.1 mmol) of 4-anisidine in 120 ml of anhydrous dichloromethane, and the mixture is stirred at 23° C. for 4 hours. The residue obtained after filtration and removal of solvent is recrystallised from n-hexane. 15.9 g (74.9 mmol, 92%) of the title compound are isolated.

$^1$H-NMR (CDCl3$_3$): d=3.83 (3H), 6.95 (2H), 7.29 (2H), 7.73 (2H), 8.47 (1H), 8.73 (2H) ppm.

EXAMPLE 2

3'-Desphenyl-3'-(4-pyridyl)-3'-N-debenzoyl-3'-N-methoxycarbonyl-7-epi-taxol (A) and 3'-desphenyl-3'-(4-pyridyl)-2,3'-N-bisdebenzoyl-3'-N-methoxycarbonyl-taxol (B)

42 μl of a 1M solution of tetrabutylammonium fluoride in tetrahydrofuran are added at 3° C., under an atmosphere of dry argon, to a solution of 15 mg (13.9 μmol) of the compound prepared in accordance with Example 1a in 0.5 ml of anhydrous tetrahydrofuran, and the mixture is stirred for 30 minutes at 3° C., heated to 23° C. and stirred for a further 30 minutes. The mixture is poured into a saturated sodium hydrogen carbonate solution, extraction is carried out with dichloromethane, the organic extract is concentrated and the residue is purified by chromatography on two analytical thin-layer plates. A mixture of ethyl acetate and methanol is used as mobile phase, and a mixture of dichloromethane and methanol is used as eluting agent.

3.8 mg (4.7 μmol, 34%) of the title compound A, 2.4 mg (3.4 μmol, 25%) of the title compound B and also 1.2 mg (1.5 μmol, 11%) of the compound described in Example 1 are isolated.

¹H-NMR (CDCl₃) of A: d=1.18 (3H), 1.23 (3H), 1.68 (3H), 1.71 (1H), 1.80 (1H), 1.83 (3H), 2.15–2.48 (4H), 2.21 (3H), 2.49 (3H), 3.56 (3H), 3.71 (1H), 3.92 (1H), 4.37 (2H), 4.63 (1H), 4.71 (1H), 4.91 (1H), 5.37 (1H), 5.67 (1H), 5.76 (1H), 6.34 (1H), 6.81 (1H), 7.33 (2H), 7.51 (2H), 7.61 (1H), 8.16 (2H), 8.63 (2H) ppm.

EXAMPLE 3

3'-Desphenyl-3'-(4-pyridyl)-3'-N-debenzoyl-3'-N-methoxycarbonyl-10-desacetyl-taxol 20.4 μl of 4N hydrochloric acid are added, under an argon atmosphere, to a solution of 9.0 mg (10.2 μmol) of compound A prepared in accordance with Example 3a in 0.8 ml of ethanol and 0.2 ml of tetrahydrofuran, and the reaction mixture is stirred at 23° C. for one hour. The addition of hydrochloric acid is repeated a further twice, each time after one hour's stirring, a saturated sodium hydrogen carbonate solution is added, extraction is carried out with dichloromethane, the organic extract is concentrated and the residue is purified by chromatography on two analytical thin-layer plates. A mixture of ethyl acetate and ethanol is used as mobile phase, and a mixture of dichloromethane and methanol is used as eluting agent 6.5 mg (8.5 μmol, 83%) of the title compound are isolated.

¹H-NMR (CDCl₃): d=1.13 (3H), 1.24 (3H), 1.78 (3H), 1.83 (3H), 1.73–1.96 (3H), 2.25 (2H), 2.37 (3H), 2.60 (1H), 3.62 (3H), 3.92 (1H), 4.14–4.28 (2H), 4.20 (1H), 4.32 (1H), 4.69 (1H), 4.94 (1H), 5.21 (1H), 5.36 (1H), 5.68 (1H), 5.83 (1H), 6.30 (1H), 7.34 (2H), 7.50 (2H), 7.62 (1H), 8.10 (2H), 8.61 (2H) ppm.

EXAMPLE 3a

3'-Desphenyl-3'-(4-pyridyl)-3'-N-debenzoyl-3'-N-methoxycarbonyl-7-triethylsilyl-10-desacetyl-taxol (A) and 3'-Desphenyl-3'-(4-pyridyl)-2,3'-N-bisdebenzoyl-3'-N-methoxycarbonyl-7-triethylsilyl-10-desacetyl-taxol (B)

25 mg (23 μmol) of the crude product prepared in accordance with Example 3b are reacted at −10° C. analogously to Example 1 and, after working up and purification, 9.0 mg (10.2 μmol, 44%) of the title compound A, 2.5 mg (3.2 μmol, 14%) of the title compound B and also 2.2 mg (2.9 μmol, 12%) of the title compound of Example 3 are isolated.

¹H-NMR (CDCl₃) of A: d=0.43–0.67 (6H), 0.94 (9H), 1.13 (3H), 1.24 (3H), 1.70 (1H), 1.76 (3H), 1.87 (3H), 1.93 (1H), 2.24 (2H), 2.36 (3H), 2.48 (1H), 3.62 (3H), 3.87 (1H), 4.18 (1H), 4.29 (1H), 4.34 (1H), 4.68 (1H), 4.91 (1H), 5.12 (1H), 5.36 (1H), 5.63 (1H), 5.77 (1H), 6.29 (1H), 7.33 (2H), 7.49 (2H), 7.60 (1H), 8.10 (2H), 8.60 (2H) ppm.

¹H-NMR (CDCl₃) of B: d=0.45–0.64 (6H), 0.94 (9H), 1.02 (3H), 1.25 (4H), 1.67 (1H), 1.72 (3H), 1.82 (3H), 1.88–2.12 (2H), 2.18 (4H), 2.47 (1H), 3.50 (1H), 3.67 (1H), 3.70 (3H), 3.90 (1H), 4.26 (1H), 4.30 (1H), 4.59 (1H), 4.61 (1H), 4.66 (1H), 4.91 (1H), 5.03 (1H), 5.27 (1H), 5.65 (1H), 6.25 (1H), 7.32 (2H), 8.62 (2H), ppm.

EXAMPLE 3b

2'-Triisopropylsilyl-3'-desphenyl-3'-(4-pyridyl)-3'-N-debenzoyl-3'-N-methoxycarbonyl-7-triethylsilyl-10-desacetyl-taxol 0.23 ml of hydrazinium hydroxide is added, under an argon atmosphere, to a solution of 25 mg (23.2 μmol) of the compound prepared in accordance with Example 1a in 1.2 ml of ethanol, and the mixture is stirred at 23° C. for 24 hours. The mixture is poured into a saturated sodium chloride solution, extraction is carried out several times with ethyl acetate and drying is carried out over magnesium sulphate. The residue obtained after filtration and removal of solvent is further reacted without being purified. 22 mg (max. 21 μmol, max. 91%) of the title compound, which still contains small amounts of starting material, are isolated.

The following Application Examples substantiate the biological activity of the compounds according to the invention without limiting their application to those Examples.

Application Example 1

Isolation and Purification of Tubulin

Bovine brains (each 330 g) are removed from freshly opened cows' heads and are transported in ice-cooled PM4-M buffer. Each brain is freed of the meninges and also of any thrombi and is homogenised with sufficient PM4M buffer in a cooling chamber. The homogenised material from 2 bovine brains is made up to a total volume of 1.0 liter with a total of 500 ml of buffer and is subjected to a first centrifugation (GSA rotor, 15 minutes, 4° C., 6500 g). The supernatant is freed of the sebaceous skin on the surface, filtered over 4 layers of thin muslin, transferred into counter-balanced centrifuge tubes (420 ml) and centrifuged again (Ti 45 rotor, 96000 g, 75 minutes, 4° C.). The supernatant is removed by pipette through the pellet and filtered over 6 layers of thin muslin, and a 50 mM GTP solution in 0.001M bicarbonate/PBS is added to obtain a final concentration of 1 mM. A first polymerisation is carried out in counter-balanced centrifuge tubes for 45 minutes in a water bath warmed to 37° C. The microtubules that have formed are removed by centrifugation (Ti 45 rotor, 27° C., 96000 g, 60 minutes), the supernatant is carefully removed by pipette and the very soft, opalescent pellet is carefully separated from the wall with a spatula. 40 ml of cold PM buffer are then added to the pellet, followed by homogenisation using a small glass mortar and incubation overnight (from 12 to 16 hours) on ice in counter-balanced centrifuge tubes in a cooling chamber. The depolymerisation product is removed by centrifugation in the Ti 60 rotor (4° C.; 96000 g, 60 minutes) and the supernatant is diluted with PM8-M buffer to 1:1, incubated in counter-balanced centrifuge tubes at 37° C. for 45 minutes and centrifuged again (Ti 45 rotor, 27° C., 96000 g, 60 minutes). The supernatant is carefully removed by pipette and the very soft opalescent pellet is taken up in 20 ml of cold PM buffer, homogenised carefully using a small glass mortar and incubated on ice for 30 minutes. The renewed centrifugation (Ti 60 rotor, 4° C., 96000 g, 60 minutes) gives tubulin, the protein content of which is determined according to Pearce or according to a photometric measurement at 280 nm. In the protein determination, dilutions of isolated material to PM buffer of 1:10, 1:20 and 1:40 are used. The PM buffer has own extinction and is deducted as a zero value from the determined protein content. The isolated material is diluted with PM buffer to the intended protein concentration (2 mg/ml).

Application Example 2

Biological effect on tubulin of 3'-desphenyl-3'-(4-pyridyl)-3'-N-debenzoyl-3'-N-methoxycarbonyl-taxol The measurement of the polymerisation of tubulin and the depolymerisation of microtubules is carried out by photometry. Before the measurement, the tubulin prepared in accordance with Application Example 1 is thawed and degassed for 15 minutes. The photometer is set to a wavelength of 350 nm. 3 μl of solvent/sample, 6 μl of GTP (0–25 μmol/l final.) and 291 μl of tubulin (2 mg protein/ml) are pipetted into the dry and cleaned dishes (10 mm). The sample is carefully stirred (without causing air bubbles), immediately placed in dish carriages and the measuring operation is started at 37° C. Once the polymerisation maximum has been reached (solvent control and taxol 1E-5 mol/l after 20 minutes), the depolymerisation is initiated by reducing the temperature to 15° C. The measuring operation is stopped at the end of the depolymerisation and the course of the change in absorption is represented in graph form as a function of time and temperature (see FIG. 1).

Figure 1:
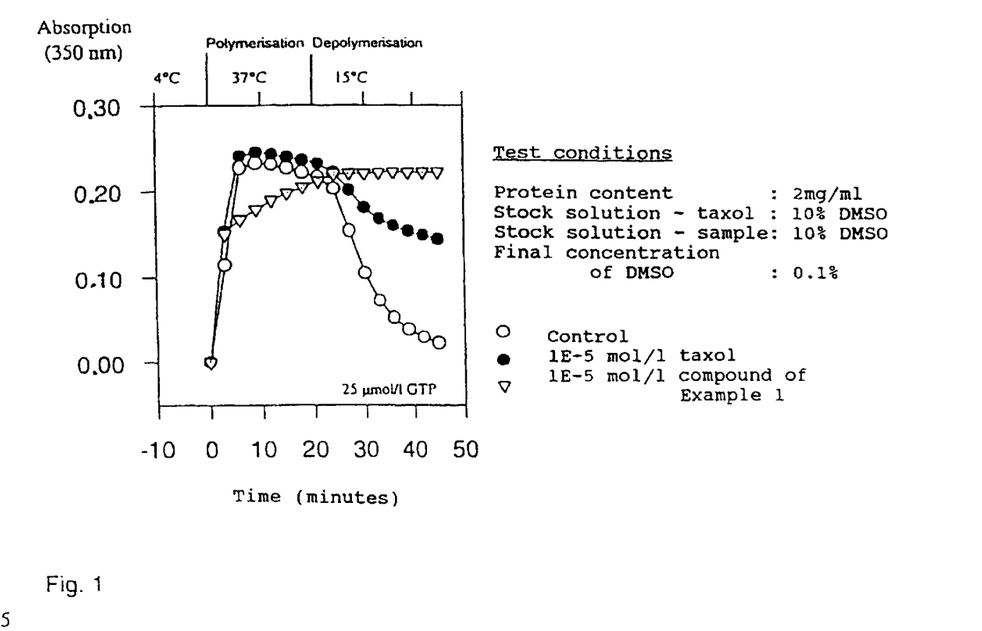
FIG. 1 shows the course of the change in absorption as a function of time and temperature (3'-desphenyl-3'-(4-pyridyl)-3'-N-debenzoyl-3'-N-methoxycarbonyl-taxol, Application Example 2).

The Figure clearly shows that taxol speeds up the polymerisation of tubulin in comparison with the control and inhibits depolymerisation, whilst the compound according to the invention 3'-desphenyl-3'-(4-pyridyl)-3'-N-debenzoyl-3'-N-methoxycarbonyl-taxol inhibits the polymerisation and stabilises the microtubules that have formed distinctly better than taxol.

Application Example 3

Figure 2:
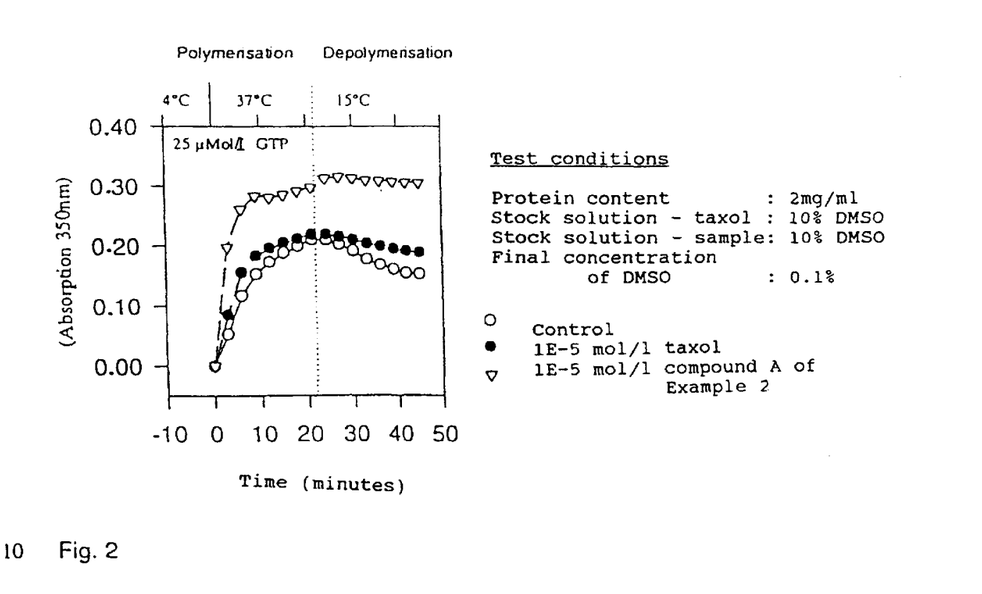
FIG. 2 shows the course of the change in absorption as a function of time and temperature (3'-desphenyl-3'-(4-pyridyl)-3'-N-debenzoyl-3'-N-methoxycarbonyl-7-epi-taxol, Application Example 3).

Biological effect on tubulin of 3'-desphenyl-3'-(4-pyridyl)-3'-N-debenzoyl-3'-N-methoxycarbonyl-7-epi-taxol 3'-Desphenyl-3'-(4pyridyl)-3'-N-debenzoyl-3'-N-methoxycarbonyl-7-epi-taxol causes a much more pronounced acceleration of the polymerisation of tubulin and stabilises the microtubules that have formed very much better than taxol. The results are shown in FIG. 2.

Application Example 4

Figure 3:
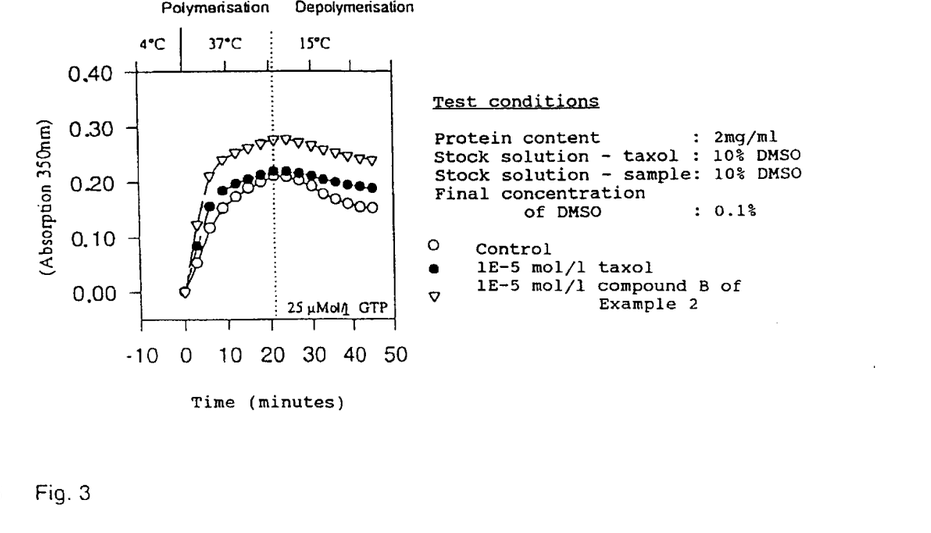
FIG. 3 shows the course of the change in absorption as a function of time and temperature (3'-desphenyl-3'-(4-pyridyl)-2,3'-N-bisdebenzoyl-3'-N-methoxycarbonyl-taxol, Application Example 4).

Biological effect on tubulin of 3'-desphenyl-3'-(4-pyridyl)-2,3'-N-bisdebenzoyl-3'-N-methoxycarbonyl-taxol 3'-Desphenyl-3'-(4-pyridyl)-2,3'-N-bisdebenzoyl-3'-N-methoxycarbonyl-taxol causes a much more pronounced acceleration of the polymerisation of tubulin and stabilises the microtubules that have formed better than taxol. The results are shown in FIG. 3.

Application Example 5

Figure 4:
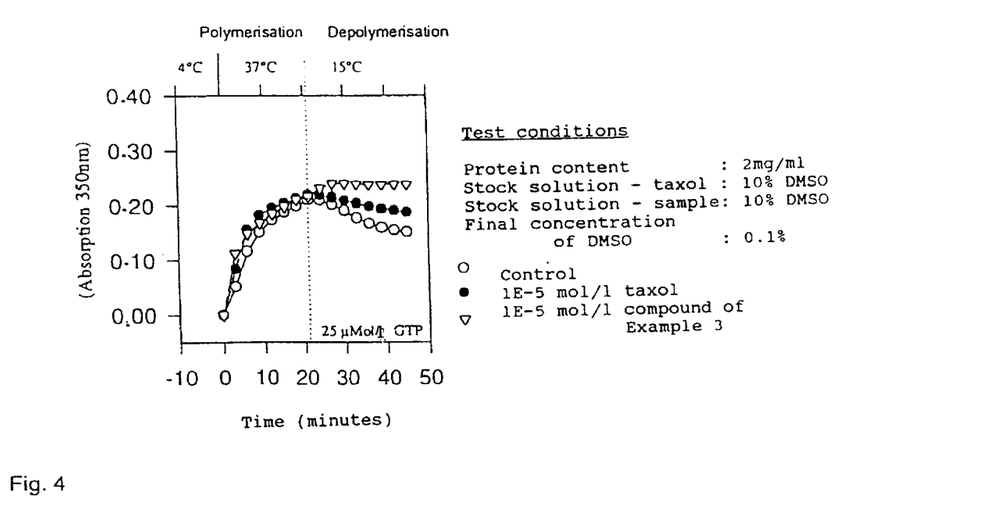
FIG. 4 shows the course of the change in absorption as a function of time and temperature (3'-desphenyl-3'-(4-pyridyl)-3'-N-debenzoyl-3'-N-methoxycarbonyl-10-esacetyl-taxol, Application Example 5).

Biological effect on tubulin of 3'-desphenyl-3'-(4-pyridyl)-3'-N-debenzoyl-3'-N-methoxycarbonyl-10-desacetyl-taxol 3'-Desphenyl-3'-(4-pyridyl)-3'-N-debenzoyl-3'-N-methoxycarbonyl-10-desacetyl-taxol does not differ from taxol in respect of the polymerisation behaviour of tubulin, but it does stabilise the microtubules that have formed substantially better than taxol. The results are shown in FIG. 4.

Application Example 6

Anti-proliferative effect on tumour cell lines of:

3'-desphenyl-3'-(4-pyridyl)-3'-N-debenzoyl-3'-N-methoxycarbonyl-taxol (1),

3'-desphenyl-3'-(4-pyridyl)-3'-N-debenzoyl-3'-N-methoxycarbonyl-7-epi-taxol (2), 3'-desphenyl-3'-(4-pyridyl)-2,3'-N-bisdebenzoyl-3'-N-methoxycarbonyl-taxol (3) and 3'-desphenyl-3'(pyridyl)-3'-N-debenzoyl-3'-N-methoxycarbonyl-10-desacetyl-taxol (4)

MDA MB 435 mammary carcinoma cells (5000 cells/well) are placed in microtitre plates (day 0, RPMI medium, 1% non-essential amino acids, 1% pyruvate, 10% foetal calf serum). The addition of the substance in several concentrations is carried out on day 1. The anti-proliferative effect is determined on day 3 using the MTT method. The $IC_{50}$ values are determined therefrom. The results are shown in Table 1.

TABLE 1

| Compound | MDA-MB 435 cells $IC_{50}$ [nM] |
|---|---|
| 1 | 2.0 |
| 2 | 0.8 |
| 3 | 8000 |
| 4 | 60 |
| Taxol (reference) | 3 |

3'-Desphenyl-3'-(4-pyridyl)-3'-N-debenzoyl-3'-N-methoxycarbonyl-taxol demonstrates an activity similar to that of taxol, whilst 3'-desphenyl-3'-(4-pyridyl)-3'-N-debenzoyl-3'-N-methoxycarbonyl-7-epi-taxol demonstrates a significantly improved inhibiting activity compared with taxol.

What is claimed is:

1. A taxane of the formula I:

wherein

Sk is $R^1$ is hydrogen or $C_1$–$C_{10}$acyl, $R^2$ is α-OH, $R^3$ is $C_1$–$C_{10}$alkyl, X-substituted phenyl, or $C_1$–$C_{10}$alkoxy, X is hydrogen, halogen, —$N_3$ or —CN, or a physiologically acceptable salt thereof, or phosphate or sulfate ester thereof, or ester or ether thereof with a physiologically acceptable water-soluble polymer, or a α-, β- or γ-cyclodextrin clathrate thereof.

2. 3'-Desphenyl-3'-(4-pyridyl)-3'-N-debenzoyl-3'-N-methoxycarbonyl-7-epi-taxol according to claim 1.

3. 3'-Desphenyl-3'-(4-pyridyl)-3'-N-debenzoyl-3'-N-methoxycarbonyl-10-desacetyl-taxol according to claim 1.

4. Process for the preparation of taxane derivatives of the formula I according to claim 1, wherein an alcohol of the formula II wherein $R^1$ and $R^2$ are as defined hereinabove and hydroxy groups contained in II are optionally protected, is reacted with a compound of the general formula IIa, IIIb or IIIc, wherein $R^3$ is as defined hereinabove and X' may be hydroxy, O-alkyl or halogen, and wherein free hydroxy groups are protected by etherification or esterification, to form compounds of the general formula I in which free hydroxy groups may be functionally modified further by etherification or esterification.

5. A taxane of the formula I:

wherein

Sk is $R^1$ is hydrogen or $C_1$–$C_{10}$acyl, $R^2$ is α-OH, $R^3$ is $C_1$–$C_{10}$alkyl, X-substituted phenyl, or $C_1$–$C_{10}$alkoxy, X is halogen, —$N_3$ or —CN, or a physiologically acceptable salt thereof, or phosphate or sulfate ester thereof, or a α-, β- or γ-cyclodextrin clathrate thereof.

6. A pharmaceutical composition comprising a compound of claim 1 and a pharmaceutically acceptable carrier.

7. A method of inhibiting the growth of neoplastic cells comprising administering to a patient in need thereof, an effective amount of a compound of claim 1.

8. A method of claim 7 comprising treating a patient in need thereof who is suffering from an ovarian, stomach, colonic, adeno, breast, lung, head or neck carcinoma, a malignant melanoma or acute lymphocytic or myelocytic leukemia.

9. A pharmaceutical composition of claim 6 wherein said compound is encapsulated within a liposome.

* * * * *